(12) United States Patent
Ho et al.

(10) Patent No.: US 7,173,159 B2
(45) Date of Patent: Feb. 6, 2007

(54) METHOD FOR SYNTHESIZING TFPX

(75) Inventors: Chan-Yuan Ho, Hsinchu (TW);
Tsair-Feng Lin, Bade (TW);
Chun-Hsu Lin, Taipei (TW);
Shieh-Jun Wang, Taipei (TW)

(73) Assignee: Yuan-Shin Materials Technology Corp., Taipei (TW)

( * ) Notice: Subject to any disclaimer, the term of this patent is extended or adjusted under 35 U.S.C. 154(b) by 51 days.

(21) Appl. No.: 11/189,710

(22) Filed: Jul. 27, 2005

(65) Prior Publication Data

US 2006/0211895 A1    Sep. 21, 2006

(30) Foreign Application Priority Data

Mar. 21, 2005    (TW) .............................. 94108585 A

(51) Int. Cl.
*C07C 22/08*    (2006.01)
(52) U.S. Cl. ...................... 570/145; 570/143; 570/144
(58) Field of Classification Search ................ 570/145, 570/144, 143
See application file for complete search history.

(56) References Cited

U.S. PATENT DOCUMENTS

| | | | |
|---|---|---|---|
| 3,878,246 | A | 4/1975 | Mathey et al. |
| 5,210,341 | A | 5/1993 | Dolbier, Jr. et al. |
| 5,536,892 | A | 7/1996 | Dolbier, Jr. et al. |
| 5,841,005 | A | 11/1998 | Dolbier, Jr. et al. |
| 5,849,962 | A | 12/1998 | Dolbier, Jr. et al. |
| 6,043,397 | A | 3/2000 | Teshima et al. |
| 6,150,499 | A | 11/2000 | Dolbier, Jr. et al. |
| 6,222,064 | B1 | 4/2001 | Lal et al. |
| 6,284,933 | B1 * | 9/2001 | Dolbier et al. .............. 570/145 |
| 7,115,788 | B2 * | 10/2006 | Jong et al. .................. 570/143 |

FOREIGN PATENT DOCUMENTS

EP    0930287    7/1999
WO    WO 98/24743    6/1998

OTHER PUBLICATIONS

S. A. Fuqua et. al.; *Synthesis And Chemistry Of Several Fluorinated p-Xylenes Designed As Precursors For α, α, α', α'-Tetraluoro-p-Xylylene*; 1964; Tetrahedron, vol. 20, pp. 1625-1632.
Leslie Dolby-Glover; *Fluoroorganic compounds in industry: applications and synthesis*; Aug. 4, 1986; Chemistry and Industry, pp. 518-523.
James H. Clark et. al.; *The Synthesis of Organofluorine Compounds Using Potassium Fluoride-Tetraphenylphosphonium Bromide Systems*; 1987, Tetragedron Letter, Bol. 28, No. 1, pp. 111-114.
Yasuo Yoshida et. al.; *A Convenient Synthesis of Fluorobenzaldehydes by KF/Ph₄PBr/18-Crown-6 Reagent System*; 1988, Chemistry Letters, pp. 1355-1358.
Naoto Yazawa et. al.; *Tetraphenylphosphonium Bromide Catalyzed Flurodenitrations and Fluorodesulfonylations. Efficient Syntheses of m-Fluoroaromatic Compounds*; 1989; Chemistry Letters; pp. 2213-2216.
R. Eric Banks; *'Halex' Fluorination of Chlorinated Benzaldehydes And Benzoyl Chlorides*; 1990; Journal of Fluorine Chemistry, pp. 529-537.
Pinaki S. Bhadury et. al.; *A facile synthesis of organofluorine compounds using a semi-molten mixture tetrabutylammonium bromine and an alkali metal fluoride*; 1995; Journal of Fluorine Chemistry, pp. 185-187.
Yoel Sasson et. al.; *Tetramethylammonium chloride as a selective and robust phase transfer catalyst in a solid-liquid halex reaction: the role of water*; 1996; Chem. Commun., pp. 297-298.
William R. Dolbier, Jr. et. al.; *A New and Practical Synthesis of Octafluorol[2.2]paracyclophane*; 1997, J. Org. Chem, pp. 7500-7502.

* cited by examiner

*Primary Examiner*—Elvis O. Price
(74) *Attorney, Agent, or Firm*—Bacon & Thomas, PLLC

(57) ABSTRACT

A method for the synthesis of TFPX (α, α, α', α'-tetrafluoro-p-xylene) is disclosed, which comprises the following steps: (a) providing a sulpholane solution comprising TCPX (α, α, α', α'-tetrachloro-p-xylene); (b) mixing the sulpholane solution with alkali metal fluoride, and phase transfer catalyst to form a mixture, wherein the phase transfer catalyst is quaternary phosphonium salt; and (c) heating the mixture.

12 Claims, No Drawings

METHOD FOR SYNTHESIZING TFPX

BACKGROUND OF THE INVENTION

1. Field of the Invention

The present invention relates to a synthesis method and, more particularly, to a synthesis method for preparing TFPX (tetrafluoro-p-xylene).

2. Description of Related Art

Because parylene polymer possess numerous advantages for manufacturing purposes, for example, maintaining the coating environment at room temperature, no residual stress resulting after coating and allowing precise controls on the thickness of the depository film along with parylene polymer's uniformity, excellent acid and alkali resistance and low dielectric properties, parylene polymer has been widely employed in the practice of electric insulation on printing electric circuit boards, damp-proofing on sensors or medical equipment, preventing corrosion on metal coating, etc. Presently the highly anticipated fluoro parylene polymer, noted for its low dielectric constant and high melting point, will be utilized in dielectric coating in the electrical and coating industries.

Fluoro parylene polymer has the structure (1) as follows:

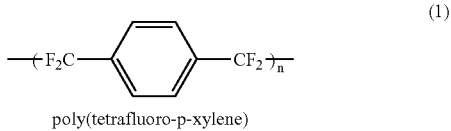

poly(tetrafluoro-p-xylene)

Fluoro parylene polymer generally is coated on products by means of chemical vapor deposition in a vacuum state at room temperature. Products coated with parylene polymer possess not only excellent anticorrosive, damp-proof and insulating characteristics, but also have the advantages of being extra-thin, transparent and poreless. Parylene polymer coating is to polymerize the more active monomer on the surface of the object. Unlike the general steps of liquid coating process, this coating process has the polymer (dimer) vaporized first, and the dimer (para-xylylene) bonds are cleaved to yield monomer radical at pyrolysis condition, whereafter it is finally polymerized to form parylene polymer.

Moreover, fluoro parylene polymer's dielectric constant decreases as the quantity of fluorine atoms increases within the polymer, thus octafluoro-2,2-paracyclophane, which is generally used nowadays, has the following structure (2):

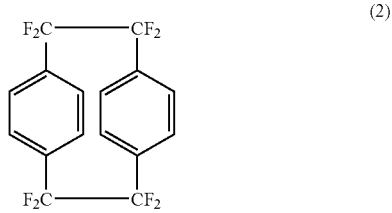

TFPX ($\alpha$, $\alpha$, $\alpha'$, $\alpha'$-tetrafluoro-p-xylene), as the molecular structure below shows, is a critical starting material in the process of synthesis for the above dimer.

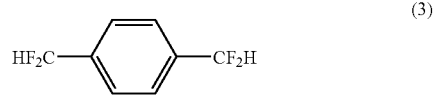

However, the TFPX synthesis method nowadays is relatively costly, time-consuming and unable to be mass-produced. For example, although TFPX can be obtained from the preparation by mixing TCPX ($\alpha$, $\alpha$, $\alpha'$, $\alpha'$-tetrachloro-p-xylene) with KF at proper ratio in either an open or closed reaction container, reacting continuously for 12 hours at a temperature of 260° C.~280° C., a lack of solutions in the reaction will cause a serious gelation problem, similar to what would happen in a solid-state reaction. Such a problem not only hinders the yield of the desired product, it yet further affects the possibility of production expansion. Other typical synthesis methods involve organic compounds comprising carbonyl group, such as terephthaldehyde, to be fluorinated with fluorinating reagents, for example $SF_4$, $MoF_6$, DAST or HF/Py at proper conditions. Although a better yield of TFPX can be achieved from such preparation, the price of the above-mentioned fluorinating reagents can be rather high. The equipments and preparation conditions can also be relatively unique and complicated, and the leftover gases and liquid wastes are difficult to deal with, thereby greatly raising the cost of preparing TFPX and thus making these methods unfavorable with respect to mass production.

Therefore, it is desirable to provide a safe, cost-effective and efficient synthesis method, such that a reduction in the cost of preparing TFPX can play a positive role in production expansion.

SUMMARY OF THE INVENTION

The present invention discloses a method for synthesizing TFPX ($\alpha$, $\alpha$, $\alpha'$, $\alpha'$-tetrafluoro-p-xylene), which comprises the following steps: (a) providing a sulpholane or its derivative solution comprising TCPX ($\alpha$, $\alpha$, $\alpha'$, $\alpha'$-tetrachloro-p-xylene); (b) mixing the sulpholane or its derivates solution with alkali metal fluorides and a phase transfer catalyst to form a mixture, wherein the phase transfer catalyst (PTC) is quaternary phosphonium salt, and the alkali metal fluorides can be KF, CsF, NaF or LiF.; and (c) heating said mixture to obtain a product. That is, the method of the present invention is to utilize sulpholane or its derivates as a solvent, within which TCPX, KF and PTC are mixed, allowing the heterogeneous-phase fluorination to take place in the solvent. Since TFPX is prepared by the solvent method of the present invention as mentioned above, the gelation issue, which is derived from the dry solid-phase reaction, shall not be a concern and production expansion is viable.

In the method of the present invention, the alkali metal fluoride can be any alkali metal fluoride most commonly used for fluorination, preferably KF, CsF, NaF or LiF. In the method of the present invention, the heating temperature in step (c) is above 100° C., preferably between 100° C. to 200° C. Also in the method of the present invention, the heating time is from 20 to 76 hours, preferably in the range of 24 to 48 hours. The method of the present invention further comprises an optional step (d) to clean the said product, preferably with acetone. Also, the method of the present invention further comprises an optional step (e) to dissolve TFPX from the said product, preferably by filtering firstly and separating TFPX apart from the product through distillation. In the method of present invention, the molar ratio of alkali metal fluoride to TCPX is in the range from 1 to 16, preferably from 4 to 8. In the method of present invention, the weight ratio of quaternary phosphonium salt to TCPX can be in the range of 3% to 20%, preferably between 3% and 10%.

Moreover, the PTC used in the method of present invention is quaternary phosphonium salt that has the structure (4) as follows:

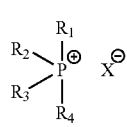

(4)

wherein the X is Cl, Br or I, and $R_1$, $R_2$, $R_3$ and $R_4$ are alkyl group, aryl group, or the combination thereof. This alkyl group is preferably $C_1$ to $C_8$ alkyl group, and the aryl group is preferably phenyl group or benzyl group. Hence, $R_1$, $R_2$, $R_3$ and $R_4$ of the quaternary phosphonium salt in the present invention can preferably be the same alkyl group, the same aryl group, different alkyl group or different aryl group. The quaternary phosphonium salt can be $(Ph)_4PBr$, $(C_4H_9)_4PBr$ or $(Ph)_3CPPh_3Cl$.

DETAILED DESCRIPTION OF THE PREFERRED EMBODIMENT

The preferred embodiment of the present invention utilizes slupholane or its derivatives, such as 2,4-dimethylsulpholane, as the solvent, whereas in the comparative examples p-xylene, DPM, DMAC, DMF, NMP and benzonitrile are each utilized as an solvent, in which the comparison of their products, quantity of PTC consumed, conditions of the reactions (temperature and time) and respective yields are organized in a table as shown in Table 1. Refer to Example 1 and Comparative Example 1 as follows for a detailed description of the embodiment.

EXAMPLE 1

Using Sulpholane as Solvent

The TFPX is prepared by first grinding KF into fine powder and drying at 160° C. (or grinding industrial-grade KF by a ball mill and drying at 210° C.) and taking 320 grams of KF and 160 grams of TCPX in a 1000 ml glass container (at a molar ratio of TCPX to KF 1:8). After that, 8 grams of PTC (tetraphenylphosphonium chloride) and 320 grams of sulpholane are added within a nitrogen atmosphere, forming a slurry state. Then, stirring in an oil bath, the slurry is heated to 160° C., such that the reaction is continued for 48 hours (meanwhile the supply of nitrogen can be discontinued). As the reaction comes to an end, the slurry is cooled and cleansed with acetone. After the slurry has been filtered, a TFPX/acetone/sulpholane siltrate and a KCl/KF cake are obtained. Finally acetone, TFPX and sulpholane are separated using segregated distillation, among which the product—TFPX can be obtained at a 70% yield.

COMPARATIVE EXAMPLE 1

Using DMAC (Dimethylacetamide) as Solvent

The TFPX is prepared by first grinding reagent-grade KF into fine powder and drying at 160° C. (or grinding industrial-grade KF by a ball mill and drying at 210° C.) and taking 10 grams of KF and 5 grams of TCPX in a 250 ml glass reaction container (at a molar ratio of TCPX to KF 1:8). After that, 0.5 gram of PTC (tetraphenylphosphonium chloride) and 4.38 grams of DMAC are added within a nitrogen atmosphere, forming a slurry state. Then, stirring in an oil bath, the slurry is heated to 160° C., such that the reaction is continued for 48 hours (meanwhile the supply of nitrogen can be discontinued). As the reaction comes to an end, the product, through GC analysis, is found to comprise 4F (TFPX, tetrafluoro-p-xylene), 3F (trifluoro-p-xylene), 2F (difluoro-p-xylene) and 1F (monofluoro-p-xylene), in which the following structures (5), (6), (7) and (8) present one of the states of 1F, 2F, 3F, and 4F respectively:

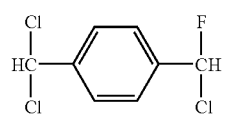

(5)

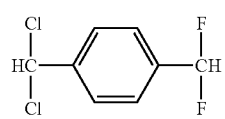

(6)

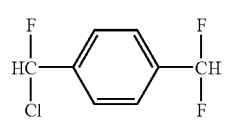

(7)

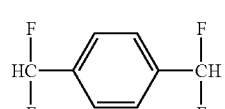

(8)

Within the product, the amounts of 4F, 3F, 2F and 1F are 20, 38, 42 and 0 respectively in terms of their GC area percentages, showing that using DMAC as a solvent to synthesize TFPX will cause products to be mostly retained at intermediates (3F and 2F), while the amount of the finished product (4F) is considerably limited and is difficult to purified by distillation as a result.

The present invention utilizes sulphoane as a solvent that allows the fluorination of TCPX to occur in a liquid state. In other words, the present invention prepares TFPX by the solvent method thereby avoiding gelation, which can be observed from the dry solid-phase reaction. Such a solvent method favors production expansion and possesses advanced utility properties for the benefit of the relevant industries.

Although the present invention has been explained in relation to its preferred embodiment, it is to be understood that many other possible modifications and variations can be made without departing from the scope of the invention as hereinafter claimed.

TABLE 1

| | TCPX | | solvent | | | reaction | | |
|---|---|---|---|---|---|---|---|---|
| | amount added(gm) | KF amount added(gm) | kind | amount add(gm) | PTC amount added(gm) | temperature (° C.) | reaction time (hr) | yield (%) |
| Comparative Example 1 | 5.00 | 10.00 | DMAC | 4.38 | 0.50(Cl) | 160~165 | 47.0 | — |
| Comparative Example 2 | 5.00 | 10.04 | Xylene | 10.31 | 0.51(Cl) | 150~155 | 49.0 | — |
| Comparative Example 3 | 4.99 | 10.05 | DPM | 6.11 | 0.50(Cl) | 160~165 | 69.0 | — |
| Comparative Example 4 | 11.24 | 22.79 | DMF | 11.17 | 1.13(Cl) | 150~155 | 50.0 | — |
| Comparative Example 5 | 25.01 | 51.27 | NMP | 47.55 | 2.51(Br) | 150~155 | 71.0 | 4.33 |
| Comparative Example 6 | 10.05 | 21.07 | Benzonitrile | 11.46 | 1.00(Br) | 155~160 | 77.0 | 20.17 |
| Example 1 | 160.11 | 320.21 | Sulpholane | 320.18 | 8.00(Br) | 155~160 | 48.0 | 67.97 |
| Example 2 | 20.26 | 40.63 | Sulpholane | 39.65 | 1.01(Br) | 155~160 | 48.0 | 57.99 |
| Example 3 | 2500.37 | 4999.9 | Sulpholane | 4121.72 | 125.1(Br) | 155~160 | 48.0 | 69.41 |
| Example 4 | 20.47 | 40.3 | 2,4-dimethyl sulpholane | 37.8 | 1.0(Br) | 153~173 | 48.0 | 40.24 |
| Example 5 | 20.74 | 40.70 | Sulpholane | 69.46 | 1.04(Bu) | 160~165 | 48.0 | 46.27 |

DPM: diphenylmethane,
DMAC: dimethylacetamide
DMF: dimethylformamide,
NMP: N-methylpyrrolidone
PTC: tetraphenylphosphonium chloride(Cl), tetraphenylphosphonium bromide(Br) tetrabutylphosphonium chloride(Bu)

What is claimed is:

1. A method for synthesizing TFPX (α, α, α', α'-tetrafluoro-p-xylene), which comprises the following steps:
   (a) providing a sulpholane or its derivates solution comprising TCPX (α, α, α', α'-tetrachloro-p-xylene);
   (b) mixing said sulpholane or its derivates solution with alkali metal fluoride and a phase transfer catalyst to form a mixture, wherein said phase transfer catalyst is quaternary phosphonium salt; and
   (c) heating said mixture to obtain a product.

2. The method of claim 1, wherein said alkali metal fluoride is KF, CsF, NaF or LiF.

3. The method of claim 1, wherein the heating temperature in step (c) is in the range of 100° C. to 200° C.

4. The method of claim 1, wherein the heating time in step (c) is in the range of 20 to 76 hours.

5. The method of claim 1, wherein further comprising a step (d) of cleansing said product.

6. The method of claim 1, wherein further comprising a step (e) of dissolving TFPX from said product.

7. The method of claim 1, wherein the molar ratio of said alkali metal fluoride to said TCPX is in the range from 1 to 16.

8. The method of claim 1, wherein the weight ratio of said sulpholane solution to said alkali metal fluoride is in the range from 0.5 to 10.

9. The method of claim 1, wherein the weight ratio of said phase transfer catalyst to said TCPX is in the range from 0.03 to 0.10.

10. The method of claim 1, wherein said quaternary phosphonium salt has the structure:

(4)

wherein X is Cl, Br or I, and $R_1$, $R_2$, $R_3$ and $R_4$ are alkyl group, aryl group, or the combination thereof.

11. The method of claim 10, wherein said alkyl group is $C_1$ to $C_8$ alkyl group, and said aryl group is phenyl group or benzyl group.

12. The method of claim 11, wherein said quaternary phosphonium salt is tetrabutylphosphonium chloride, tetraphenylphosphonium chloride or tetraphenylphosphonium bromide.

* * * * *